United States Patent
Kana et al.

(10) Patent No.: US 10,398,883 B2
(45) Date of Patent: Sep. 3, 2019

(54) COMBINATION WOUND DRAIN AND SUBSTANCE-DELIVERY SYSTEM AND METHOD

(71) Applicant: SpineSmith Partners, L.P., Austin, TX (US)

(72) Inventors: Richard J. Kana, Lexington, TX (US); Richard A. Hynes, Melbourne, FL (US)

(*) Notice: Subject to any disclaimer, the term of this patent is extended or adjusted under 35 U.S.C. 154(b) by 452 days.

(21) Appl. No.: 15/147,623

(22) Filed: May 5, 2016

(65) Prior Publication Data

US 2017/0319830 A1 Nov. 9, 2017

(51) Int. Cl.
| | | |
|---|---|---|
| *A61M 27/00* | (2006.01) | |
| *A61M 5/158* | (2006.01) | |
| *A61M 1/00* | (2006.01) | |
| *A61M 37/00* | (2006.01) | |

(52) U.S. Cl.
CPC ............ *A61M 27/00* (2013.01); *A61M 1/008* (2013.01); *A61M 5/1582* (2013.01); *A61M 37/00* (2013.01)

(58) Field of Classification Search
CPC .......... A61M 1/008; A61M 2202/0007; A61M 25/007; A61M 25/0071; A61M 27/00; A61M 5/1582; A61M 37/00; A61M 2039/1033; A61M 2039/1038; A61M 2039/1044; A61M 2039/1061; A61M 2039/261; A61M 2039/268; A61M 39/10; A61M 39/1011; A61M 39/14; A61M 39/143; A61M 39/22; A61M 39/26
See application file for complete search history.

(56) References Cited

U.S. PATENT DOCUMENTS

| 8,118,791 | B2* | 2/2012 | Flick | ................ | A61F 13/00063 |
| | | | | | 604/304 |
| 2005/0137539 | A1* | 6/2005 | Biggie | ................ | A61M 1/0088 |
| | | | | | 604/313 |
| 2010/0063463 | A1* | 3/2010 | Wiesner | .............. | A61M 1/0049 |
| | | | | | 604/313 |

* cited by examiner

*Primary Examiner* — Brandy S Lee
(74) *Attorney, Agent, or Firm* — Winstead PC

(57) ABSTRACT

A combination wound drain and substance-delivery device includes a drain portion and a substance delivery portion. The drain portion and the substance-delivery portion include interior cavities that are separated from one another to prevent fluids and/or materials disposed within the interior cavities from mixing together. Each of the interior cavities includes one or more perforations that allow fluid communication between a wound site and each of the interior cavities. The device further includes a tip coupled to the drain portion that facilitates removal of collected waste from the drain portion. The device may include an attachment mechanism that helps secure the device when placed within a wound site.

21 Claims, 3 Drawing Sheets

COMBINATION WOUND DRAIN AND SUBSTANCE-DELIVERY SYSTEM AND METHOD

TECHNICAL FIELD OF THE INVENTION

The present disclosure relates generally to the field of medicine. More particularly, it concerns a method and device for removal of waste from and application of a substance to a wound site.

BACKGROUND OF THE INVENTION

Catheters are widely used for evacuating waste from post-operative wounds, particularly deep wounds. Such deep wounds may be created during spinal or other types of surgery. These wounds need to be drained because waste accumulation inside the wound may result in pain and/or infection. Infections are not uncommon following surgeries, and, when they do occur, are costly to manage and place the patient at greater risk.

In an effort to combat infections, it is typical and normal for surgeons to apply an antibiotic or other medical substance in and around the wound site during final closure of the wound. Antibiotics are applied as a measure taken to help avoid the chance of postoperative infections. Other medical substances, such as, for example, bone marrow concentrates, may also be applied to a wound site to promote healing and regrowth of tissues. While this may be a viable and effective procedure, the antibiotic and/or medical substance will typically disperse and dilute away in a relatively short time, thus limiting its ability to properly control potential post-operative infections for an extended length of time.

Various types of drains have been developed for evacuating fluids from wounds. The suction or collection portion of the drain is placed deep within the wound and left there to drain off the excess fluids that naturally collect after surgery. Depending on the individual patient, the drain will be removed, sometimes only hours later, but can extend to several days post-surgery.

Topical application at the wound site and/or possible intravenous methods of infection control may be used to prevent post-operative infection, but the most effective treatment would be to administer antibiotics directly and deep within the wound site. Thus, it would therefore be beneficial to have a device that would serve the dual purpose of evacuation of fluids, as well providing a time-controlled delivery system for an antibiotic or other medical substance.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of claimed subject matter.

In a typical embodiment, a device for combined wound drainage and substance delivery includes a drainage portion that has a first end and a second end, an interior cavity that extends along a length of the drainage portion, a perforation disposed between the first end and the second end and adapted to allow communication of waste between the interior cavity and an area in proximity to an exterior of the drainage portion, and a tip disposed at the first end that allows waste within the interior cavity to exit the device. The device also includes a substance-delivery portion that has a first end and a second end, wherein the first end of the substance-delivery portion is adjacent to the second end of the drainage portion and an interior cavity that extends along a length of the substance-delivery portion. In a typical embodiment, the device includes a wall disposed between the drainage portion and the substance-delivery portion.

In a typical embodiment, a method for removing waste from and delivering a substance to a wound site includes inserting a substance into an interior cavity of a substance-delivery portion of a device for combined wound drainage and substance delivery and inserting the device for combined wound drainage and substance delivery into a wound site. In a typical embodiment, the device includes a drainage portion that has a first end and a second end, an interior cavity that extends along a length of the drainage portion, a perforation disposed between the first end and the second end and adapted to allow communication of waste between the interior cavity and an area in proximity to an exterior of the drainage portion, and a tip disposed at the first end that allows waste within the interior cavity to exit the device. The device also includes a substance-delivery portion that has a first end and a second end, wherein the first end of the substance-delivery portion is adjacent to the second end of the drainage portion and an interior cavity that extends along a length of the substance-delivery portion. In a typical embodiment, the device includes a wall disposed between the drainage portion and the substance-delivery portion.

In some embodiments, the combination wound drain and substance-delivery device of the instant application is capable of holding and dispensing up to about 1.0 to about 2.0 grams of antibiotics. In other embodiments, an amount of antibiotic may be increased or decreased as needed based upon a decision of the treating physician and/or the type of antibiotic being used. In some embodiments, the combination wound drain and substance-delivery device of the instant application is capable of holding and dispensing between about 0.1 milligrams and about 2.0 grams of antibiotics. In other embodiments, the device 100 may be adapted to hold more than 2.0 grams of antibiotics as desired.

In some embodiments, the combination wound drain and substance-delivery device of the instant application may be loaded during a surgical procedure with an antibiotic selected at the discretion of the surgeon.

In various embodiments, the combination wound drain and substance-delivery device of the instant application can accommodate a wide range of powdered-forms of medical preparations, and fluids that can be absorbed onto a carrier material or scaffold (e.g., bone marrow concentrate mixed with and absorbed by gelatin granules).

In various embodiments, the combination wound drain and substance-delivery device of the instant application enables a slowed or time-release of a substance that provides consistent and controlled release of a substance, such as, for example, a material like a powdered form of an antibiotic over a period of 12-36 hours. Materials absorbed onto scaffolds, such as, for example, gelatin particles, are released over several days as the gelatin is degraded.

In various embodiments, the combination wound drain and substance-delivery device of the instant application includes an attachment mechanism that aids in the device's placement into and retention in a wound site. The attachment mechanism may be, for example, a hook, a clasp, a loop, tether, clip, and the like that is adapted to secure the device to an implanted structure or a bone within the patient.

In a typical embodiment, the combination wound drain and substance-delivery device of the instant application is a one-piece design that includes a physical separation between a drainage portion and substance-delivery portion. In other embodiments, the combination wound drain and substance-delivery device could comprise a modular design in which, for example, the drainage portion and the substance-delivery portion are capable of being separated from one another.

Throughout this application, the term "about" is used to indicate that a value includes values that approximate the value described. The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1:
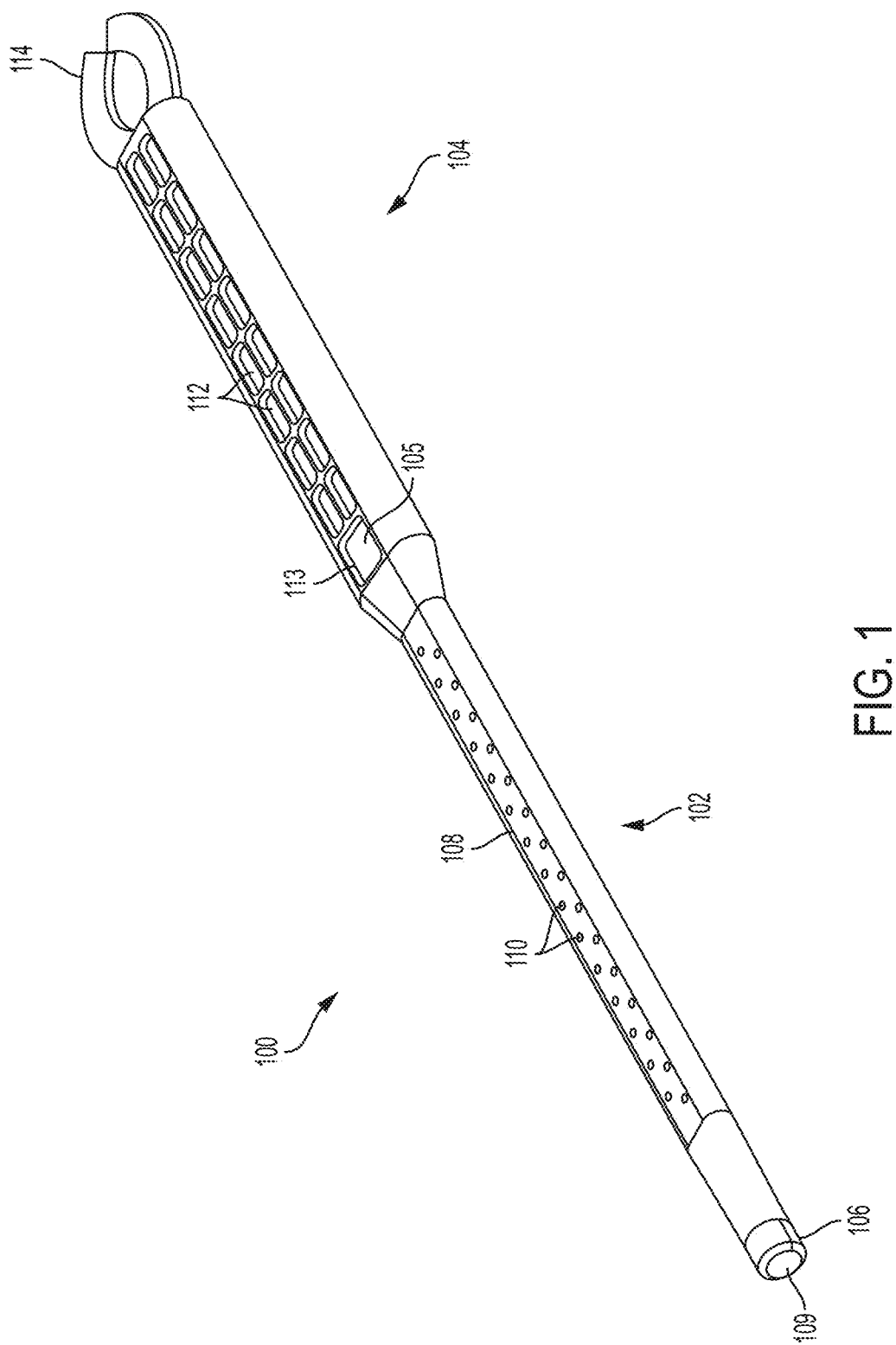
FIG. 1 is an isometric view of a combination wound drain and substance-delivery device.

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

Referring now to FIG. 1, a combination wound drain and substance-delivery device 100 is shown. In a typical embodiment, the device 100 is made from a silicon material. In other embodiments, the device 100 may be made from various soft and pliable silicon or rubber-type materials. The device 100 includes a drain portion 102 and substance-delivery portion 104. As shown in FIG. 1, the drain portion 102 and the substance-delivery portion 104 are arranged to be generally coaxial with one another. In other embodiments, other alignments/shapes may be used as desired or needed. In a typical embodiment, the device 100 is adapted to be inserted into a wound site. Orientation of the device 100 within the wound site is determined by a surgeon. In a typical embodiment, the device 100 is inserted into the wound site with such that the substance-delivery portion 104 is inserted first. When so inserted, the drain portion 102 is positioned to remove waste from the wound site via a tube or hose and the substance-delivery portion 104 is positioned to deliver one or more substances to the wound site. In a typical embodiment, the one or more substances may include, for example, antibiotics, bone marrow concentrate, concentrated plasma, and the like.

In a typical embodiment, the drain portion 102 is an elongated tube that includes a tip 106 and a perforated section 108. An interior cavity 109 is formed through the drain portion 102 and extends from the tip 106 towards the substance-delivery portion 104. In some embodiments, the drain portion 102 has an oval-shaped cross-section (e.g., see FIG. 3), though other cross-sections, such as, for example, round, square, triangular, etc., are permissible. The tip 106 is adapted to connect to a tube that enables waste that has collected within the interior cavity 109 to be removed from the drain portion 102. In some embodiments, suction may be provided via the tube to reduce a pressure within the drain portion 102 to draw waste out of the wound site.

The perforated section 108 includes a plurality of perforations 110 along a length of the perforated section 108. The plurality of perforations 110 enables waste from the wound site surrounding the drain portion 102 to enter an inside of the drain portion 102 for removal from the wound site via the tube. In some embodiments, the plurality of perforations 110 is disposed on a single side of the drain portion 102. In such embodiments, it is possible to orient the plurality of perforations 110 in a desired direction to focus a direction of waste removal. In some embodiments, the plurality of perforations 110 is disposed on two sides of the drain portion 102 (e.g., a top face and a bottom face of the drain portion 102). In some embodiments, the plurality of perforations 110 is disposed about a periphery of the drain portion 102 so that waste can enter the drain portion 102 from any direction. The plurality of perforations 110 may be of a variety of sizes depending on a particular application. In some embodiments, it may be desirable for the plurality of perforations 110 to be smaller to control a size of waste material that is drawn into the drain portion 102. In other embodiments, the plurality of perforations 110 may be larger to enable larger/more waste materials to enter the drain portion 102. As shown in FIG. 1, each of the plurality of perforations 110 is generally circular. The shape of the plurality of perforations may be changed as desired (e.g., square, rectangular, etc.).

Figure 4:
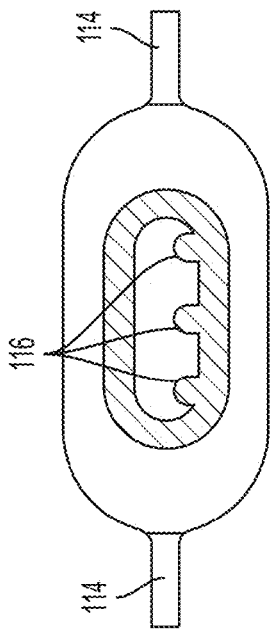
FIG. 4 is a sectional view of a drain portion of a combination wound drain and substance-delivery device.
Figure 5:
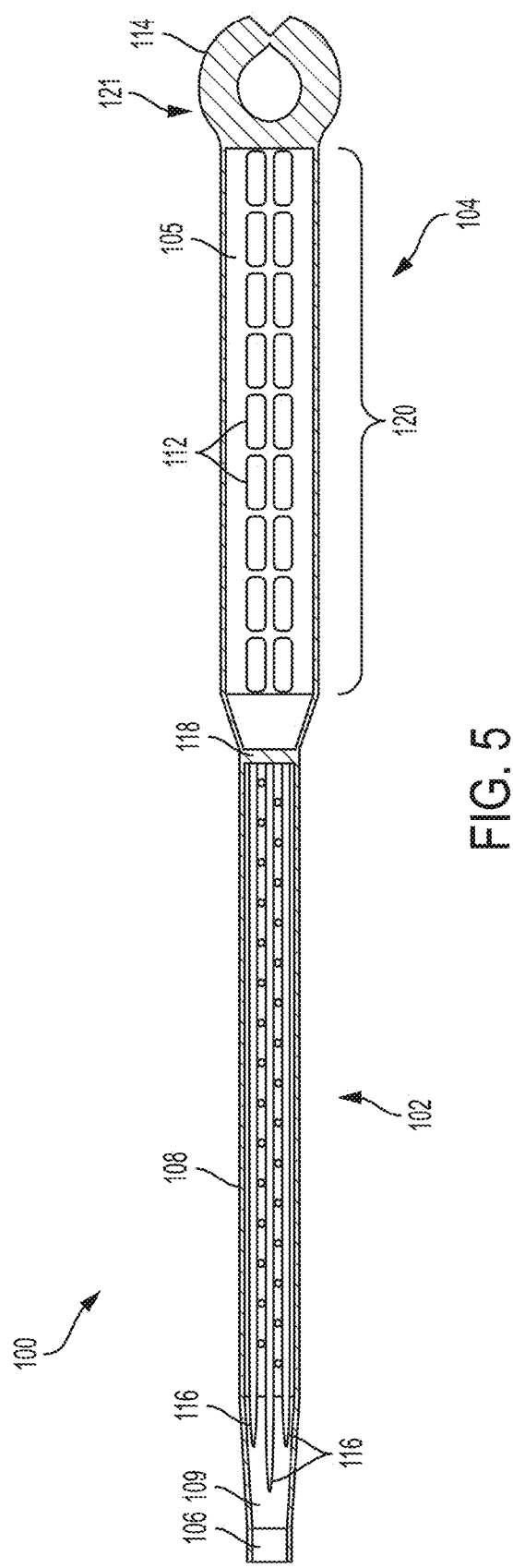
FIG. 5 is sectional view of a combination wound drain and substance-delivery device.

In a typical embodiment, the substance-delivery portion 104 is an elongated tube that includes an interior cavity 105 (best seen in FIG. 5). The interior cavity 109 of the drain portion 102 and the interior cavity 105 of the substance-delivery portion 104 are separated from one another via a wall 118 (e.g., see FIG. 5) such that substances within the interior cavities 109 and 105 are prevented from mixing together. In some embodiments, the substance-delivery portion 104 has an oval-shaped cross-section (e.g., see FIG. 4), though other cross-sections, such as, for example, round, square, triangular, etc. are permissible. In a typical embodiment, the substance-delivery portion 104 includes a plurality of perforations 112 disposed along a length of the substance-delivery portion 104. The plurality of perforations 112 enables delivery of a substance from the device 100 to the wound site surrounding the substance-delivery portion 104. In some embodiments, the plurality of perforations 112 is disposed on a single side of the substance-delivery portion 104. In such embodiments, it is possible to orient the plurality of perforations 112 in a desired direction to focus a direction of substance delivery. In some embodiments, the plurality of perforations 112 is disposed on two sides of the substance-delivery portion 104 (e.g., a top face and a bottom face of the substance-delivery portion 104). In some embodiments, the plurality of perforations 112 is disposed about a periphery of the substance-delivery portion 104 to enable delivery of the substance to the wound site in all directions. The plurality of perforations 112 may be of a variety of sizes depending on a particular application. In some embodiments, it may be desirable for the plurality of perforations 112 to be smaller to help retain a substance that has been inserted into the substance-delivery portion 104. In other embodiments, the plurality of perforations 112 may be larger to enable greater interaction between the substance-delivery portion 104 and the wound site. As shown in FIG. 1, the plurality of perforations 112 are generally rectangular. The shape of the plurality of perforations may be changed as desired (e.g., square, circular, etc.).

In some embodiments, the substance-delivery portion 104 may include a perforation 113 that facilitates insertion of a substance or material into the substance-delivery portion 104. In some embodiments, the perforation 113 may be larger than each of the plurality of perforations 112. In some embodiments, the perforation 113 may be the same size as the plurality of perforations 112.

In some embodiments, a carrier material, such as, for example, a gauze-like material or a scaffold, may be inserted into the substance-delivery portion 104 to facilitate delivery of substances to the wound site. In a typical embodiment, the carrier material may be inserted into the substance-delivery portion 104 via the perforation 113. The gauze-like material may be, for example, composed of cotton or other absorbent fabric material, and the like. The scaffold may be, for example, composed of proteins, like gelatin, collagen or synthetic polymers like poly(Lactic-co-glycolic) acid, and the like. In some embodiments, the gauze-like material facilitates a timed or slow release of the substance into the wound site. The gauze-like material can be pre-soaked with a substance, such as, for example, a hydrated medication, antibiotics, and the like. The gauze-like material holds the fluid-based medication within the drain, thereby allowing a controlled release of the substance directly into the wound site. In some embodiments, the gauze-like material is a material that is absorbed by the body (e.g., poly (Lactic-co-glycolic) acid; gelatin, etc.). In some embodiments, the gauze-like material remains within the substance-delivery portion 104 and is removed from the wound site with the device 100 when then device 100 is removed from the wound site.

In some embodiments, the gauze-like material is folded or rolled to fit within the substance-delivery portion 104. An amount of substance that can be delivered to the wound site from the substance-delivery portion 104 depends on the size of the gauze-like material and the volume of the interior cavity 105 of the substance-delivery portion 104. In a typical embodiment, up to 4 mL of solubilized substance may be delivered to the wound site in a single application of the device 100. More or less substance may be delivered by altering dimensions of the substance-delivery portion 104 and/or the type and/or amount of carrier material.

In some embodiments, a substance for delivery to the wound site may be inserted into the substance-delivery portion 104 without the use of a carrier material. In such an embodiment, the substance may have a thicker consistency (e.g., a paste or gel) to prevent the substance from quickly pouring out of the substance-delivery portion 104. In some embodiments, using a gel-like substance provides a delayed release of the substance to the wound site.

In some embodiments, the substance-delivery portion 104 may include a closeable opening to facilitate insertion and removal of a carrier material or substance. In one embodiment, the substance-delivery portion 104 comprises a hinged portion disposed along a length 120 or end 121 (see FIG. 5) of the substance-delivery portion 104 that permits the substance-delivery portion 104 to be opened for insertion of a substance or carrier material.

In some embodiments, the device 100 includes an attachment mechanism 114. The attachment mechanism 114 may be made of a pliable material, such as, for example a plastic or silicon material that is pliable. The attachment mechanism may be, for example, a hook, a clasp, a loop, tether, clip, and the like. As shown in FIG. 1, the attachment mechanism 114 is disposed on an end of the substance-delivery portion 104. The attachment mechanism 114 enables the device 100 to be attached to, for example, implanted hardware or possibly a boney structure within the patient. In some embodiments, the attachment mechanism may be secured to a portion of a patient's anatomy, such as, for example, a bone, via an absorbable suture and the like. With the attachment mechanism 114 attached to implanted hardware or a boney structure, the device 100 is lightly held in place, even if the patient is being sutured and moved about, etc. The attachment mechanism 114 is a "soft" attachment, so that when the device 100 is removed, the attachment mechanism simply releases from its attachment area and slides out with the rest of the device 100.

Figure 2A:
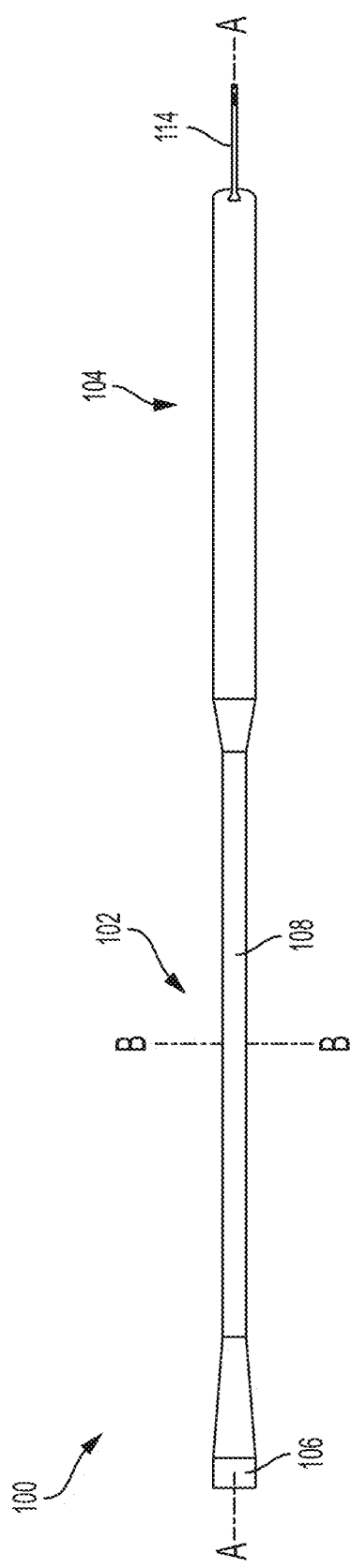
FIG. 2A is a side view of a combination wound drain and substance-delivery device.
Figure 2B:
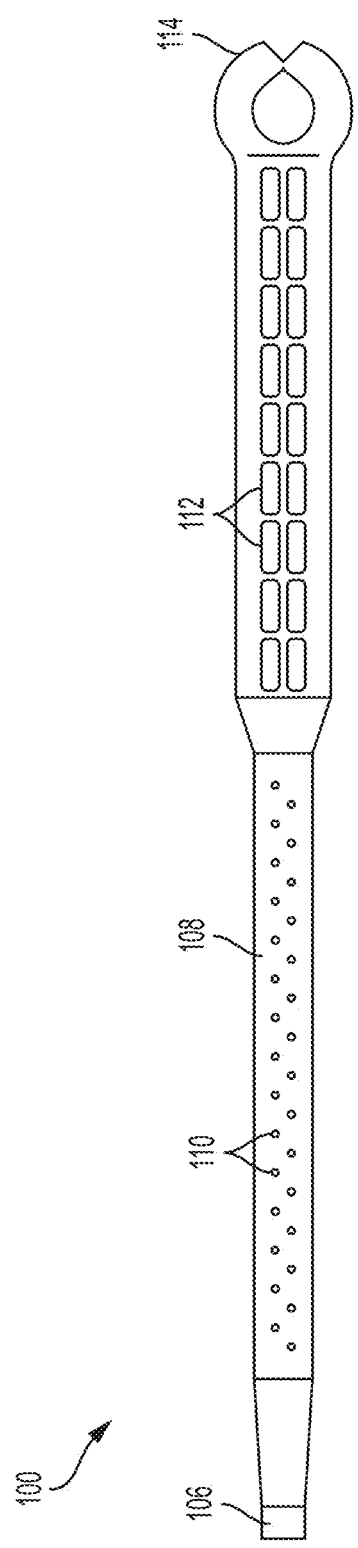
FIG. 2B is a top view of a combination wound drain and substance-delivery device.

FIGS. 2A and 2B are side and top views, respectively, of the drain 100 of FIG. 1. As shown in FIGS. 2A and 2B, the perforated section 108 and the substance-delivery portion 104 have cross-sections resembling a flattened-tube. In other embodiments, the perforated section 108 and the substance-delivery portion 104 could have other cross-sectional shapes, such as, for example, circular, triangular, square, etc. In the embodiment of FIGS. 2A and 2B, the substance-delivery portion 104 has a width and a height that is greater than a width and height of the perforated portion 108. The relative dimensions of the perforated section 108 and the substance-delivery portion 104 can be varied based on various design considerations. For example, embodiments in which a carrier material is used to deliver a substance to a wound site may result in larger dimensions for the substance-delivery portion 104, and embodiments in which a carrier material is not used may result in smaller dimensions for the substance-delivery portion 104.

Figure 3:
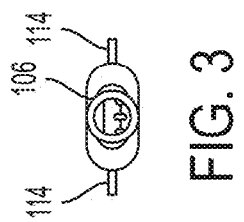
FIG. 3 is a sectional view of a tip of a combination wound drain and substance-delivery device.

As shown in FIGS. 2A and 2B, the tip 106 has a circular cross-section (also see FIG. 3). In some embodiments, using a circular cross-section allows the tip 106 to easily couple to a tube to assist with waste removal from device 100. In other embodiments, the tip 106 may have other cross-sections or features as needed to couple to various types of tubes.

Still referring to FIGS. 2A and 2B, the attachment mechanism 114 is shown as a thin and pliable piece that extends away from an end of the substance-delivery portion 104. As discussed above relative to FIG. 1, in other embodiments the attachment mechanism may be a different type of connector, such as, for example, a hook, a clasp, a loop, tether, clip, and the like.

FIG. 3 is a view looking into the tip 106 of FIG. 1. As shown in FIG. 3, an overall profile of the device 100 is slim. The slim profile facilitates placement of the device 100 within a wound site. In other embodiments, the overall profile of the device 100 may be changed to suit a specific use of the device 100. In some embodiments, instead of a relatively slim or flat profile, the device 100 may comprise other profiles, such as, for example, circular, ovular, triangular, square, and the like.

FIG. 4 is a sectional view of the drain portion 102 about section line B-B of FIG. 2A. In the embodiment shown in FIG. 4, the interior of the drain portion 102 includes a plurality of ribs 116 that extend along a length of a bottom of the interior of drain portion 102. The plurality of ribs 116 provide some increased rigidity along the length of the drain portion 102 to reduce bending and flexing of the drain portion 102. The plurality of ribs 116 additionally provide some crush prevention that prevents the drain portion 102 from collapsing as a result of, for example, application of vacuum to the drain portion 102 or from being crushed or squeezed by the wound site etc. The embodiment of FIG. 4 shows three ribs 116 disposed on a bottom side of the drain portion 102. In other embodiments, more or fewer ribs 116 could be included. In other embodiments, the plurality of ribs 116 may be located on a top side of interior of the drain portion 102 or on both the top and bottom sides of the interior of the drain portion 102. In other embodiments, one or more ribs may be included on an exterior of the drain portion 102.

FIG. 5 is a sectional view of the device 100 about section line A-A of FIG. 2A. In FIG. 5, the plurality of ribs 116 is shown extending along a length of the drain portion 102. Although three ribs 116 are shown in the embodiment of FIG. 5, the drain portion 102 may include more or fewer ribs 116 as desired. In some embodiments, lengths of the ribs 116 may be longer or shorter. In some embodiments, one or more of the ribs 116 may be segmented (i.e., one or more of the ribs 116 may include periodic gaps along its length).

WORKING EXAMPLES

A combination wound drain and substance-delivery device was assessed to determine kinetics of release of antibiotic vancomycin. Vancomycin powder (~50 mg) was placed in a syringe, connected to another syringe with concentrated plasma (~2 mL) and solubilized/suspended by passing the concentrated plasma into the syringe with the vancomycin powder to form a mixture. The mixture was then dispensed via a Y-connector along with a CaCl2/Thrombin solution at a ratio of 10:1 (vancomycin/plasma to CaCl2/Thrombin solution) into the combination wound drain and substance-delivery device. The release of vancomycin was assessed over time by placing the loaded drain into a solution and recovering aliquots periodically for analysis. Vancomycin loaded as a powder was completely released within 6 hours. In contrast, vancomycin dispersed in clotted concentrated plasma was very slowly released, such that only 0.33% of the vancomycin was released by 6 hours, with 81.3% being released by 48 hours.

In a second test, a combination wound drain and substance-delivery device was loaded with a clot that was made by forming a clot layer, placing 200 mg of vancomycin powder on the surface of the clot, and then placing another clot layer over the vancomycin, thereby sealing the powder within the two layers of concentrated plasma. The composite clotted construct was then placed within the substance-delivery portion of the combination wound drain and substance-delivery device.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A device for combined wound drainage and substance delivery, the device comprising:
   a drainage portion comprising:
      a first end and a second end;
      an interior cavity that extends along a length of the drainage portion;
      a perforation disposed between the first end and the second end and disposed on an exterior surface of the device to allow communication of waste between the interior cavity and a wound site; and
      a tip disposed at the first end that allows waste within the interior cavity to exit the device;
   a substance-delivery portion comprising:
      a first end and a second end, wherein the first end of the substance-delivery portion is adjacent to the second end of the drainage portion; and
      an interior cavity that extends along a length of the substance-delivery portion;
      and
      a perforation disposed between the first end and the second end of the substance-delivery portion and adapted to allow fluid communication between the interior cavity of the substance-delivery portion and a wound site; and
   a wall disposed between the drainage portion and the substance-delivery portion.

2. The device of claim 1, wherein the drainage portion comprises a rib disposed within the interior cavity of the drainage portion.

3. The device of claim 1, further comprising an attachment mechanism coupled to the second end of the substance-delivery portion.

4. The device of claim 3, wherein the attachment mechanism is selected from a group consisting of: a hook, a clasp, a loop, tether, and a clip.

5. The device of claim 1, further comprising a carrier material adapted for insertion into the substance-delivery portion.

6. The device of claim 5, wherein the carrier material comprises gauze.

7. The device of claim 5, wherein the carrier material is a scaffold.

8. The device of claim 1, wherein the device comprises a one-piece design.

9. The device of claim 1, wherein the device comprises a modular design that permits the drain portion to be coupled to and separated from the substance-delivery portion.

10. A method for removing waste from and delivering a substance to a wound site, the method comprising:
   inserting a substance into an interior cavity of a substance-delivery portion of a device for combined wound drainage and substance delivery;
   inserting the device for combined wound drainage and substance delivery into a wound site;
   wherein the device for combined wound drainage and substance delivery comprises:
      a drainage portion comprising:
         a first end and a second end;
         an interior cavity that extends along a length of the drainage portion;
         a perforation disposed between the first end and the second end and disposed on an exterior surface of the device to allow fluid communication between the interior cavity of the drainage portion and the wound site; and
         a tip disposed at the first end that allows waste within the interior cavity to exit the device;
      a substance-delivery portion comprising:
         a first end and a second end, wherein the first end of the substance-delivery portion is adjacent to the second end of the drainage portion; and
         an interior cavity that extends along a length of the substance-delivery portion; and
         a perforation disposed between the first end and the second end of the substance-delivery portion and adapted to allow fluid communication between the interior cavity of the substance-delivery portion and the wound site; and
      a wall disposed between the drainage portion and the substance-delivery portion.

11. The method of claim 10, wherein the inserting the substance step is performed during a surgical procedure and the substance is chosen by a user.

12. The method of claim 10, wherein the inserting the substance step further comprises inserting a carrier material that comprises the substance.

13. The method of claim 12, wherein the carrier material is selected from a group consisting of: a gauze-like material, a scaffold, and gelatin particles.

14. The method of claim 10, wherein the substance is a gel-like substance.

15. The method of claim 10, wherein the substance is time-released into the wound site over a period of 12-36 hours.

16. The method of claim 10, wherein the substance is an antibiotic.

17. The method of claim 10, wherein the substance comprises bone marrow concentrate.

18. The method of claim 10, wherein the substance comprises concentrated plasma.

19. The method of claim 10, wherein the device for combined wound drainage and substance delivery further comprises a rib disposed within the interior cavity of the drainage portion.

20. The method of claim 10, wherein the device further comprises an attachment mechanism coupled to the second end of the substance-delivery portion.

21. A device for combined wound drainage and substance delivery, the device comprising:
   a drainage portion comprising:
      a first end and a second end;
      an interior cavity that extends along a length of the drainage portion;
      a perforation disposed between the first end and the second end and adapted to allow communication of waste between the interior cavity and a wound site; and
      a tip disposed at the first end that allows waste within the interior cavity to exit the device;
   a substance-delivery portion comprising:
      a first end and a second end, wherein the first end of the substance-delivery portion is adjacent to the second end of the drainage portion; and
      an interior cavity that extends along a length of the substance-delivery portion; and
      a perforation disposed between the first end and the second end of the substance-delivery portion and disposed on an exterior surface of the device to allow fluid communication between the interior cavity of the substance-delivery portion and a wound site; and
   a wall disposed between the drainage portion and the substance-delivery portion.

* * * * *